United States Patent [19]

Lanz et al.

[11] Patent Number: 5,132,419
[45] Date of Patent: Jul. 21, 1992

[54] PROCESS FOR THE PREPARATION OF 7-AMINO-3-((Z)-1-PROPEN-1YL)-3-CEPHEM-4-CARBOXYLIC ACID

[75] Inventors: Joachim Lanz; Paul Naab; Ulrich Rosentreter, all of Wuppertal, Fed. Rep. of Germany

[73] Assignee: Bayer Aktiengesellschaft, Leverkusen, Fed. Rep. of Germany

[21] Appl. No.: 589,304

[22] Filed: Sep. 27, 1990

[30] Foreign Application Priority Data

Oct. 3, 1989 [DE] Fed. Rep. of Germany ....... 3932905
Oct. 11, 1989 [DE] Fed. Rep. of Germany ....... 3933934

[51] Int. Cl.$^5$ ............................................. C07D 501/14
[52] U.S. Cl. ...................................... 540/215; 540/230
[58] Field of Search ................ 540/219, 222, 215, 230

[56] References Cited

FOREIGN PATENT DOCUMENTS 0292806 11/1988 European Pat. Off. .
0292808 11/1988 European Pat. Off. .
2173798 10/1986 United Kingdom .

Primary Examiner—Nicholas S. Rizzo
Attorney, Agent, or Firm—Sprung Horn Kramer & Woods

[57] ABSTRACT (7-APCA) having the formula (I)

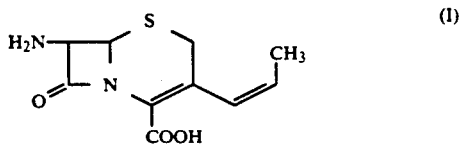

which is an important synthesis intermediate in the preparation of cephalosporin-like antibiotics, is prepared by treating a compound of the formula (II)

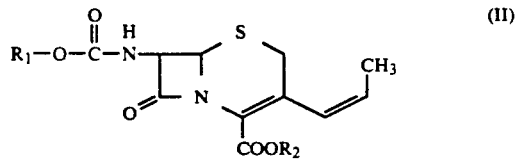

in which $R_1$ and $R_2$ represent alkyl, aryl and aralkyl radicals, with a strong protonic acid or with a Lewis acid. Compound (II) is prepared by adding triphenylphosphine and alkali metal iodide to a compound of the formula (VI)

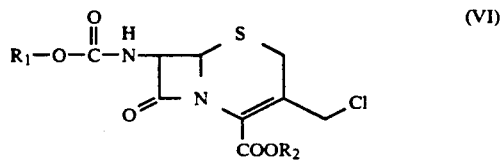

then reacting with acetaldehyde in base. Compound (VI) is prepared by treating a compound of the formula (VII)

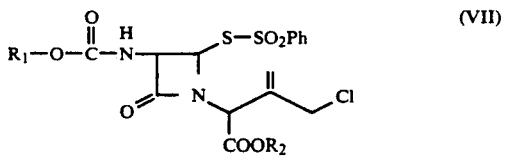

with a base in a polar solvent at $-70°$ C. to $0°$ C. Compound (VII) is prepared by treating a compound of the formula (VIII)

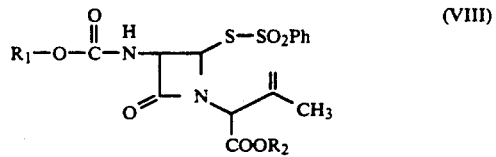

with a chlorinating agent in an organic solvent.

6 Claims, No Drawings

PROCESS FOR THE PREPARATION OF 7-AMINO-3-((Z)-1-PROPEN-1YL)-3-CEPHEM-4-CARBOXYLIC ACID

The invention relates to a process for the preparation of 7-amino-3-[(Z)-1-propen-1-yl]-3-cephem-4-carboxylic acid, which in the following is also designated as 7-APCA or as the compound (I).

7-APCA corresponds to the structural formula

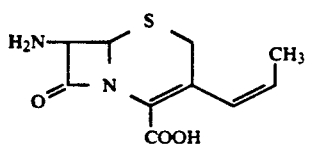

and is an important synthesis intermediate for the preparation of cephalosporin-like antibiotics. For example, 7-APCA can be converted into compounds as are described in European Patent Specifications 88 107 679.8 and 88 107 686.3.

This invention describes a simplified process for the preparation of the compound (I). In this connection, compounds of the general formula (II) are converted to (I) in a single synthesis step according to the equation

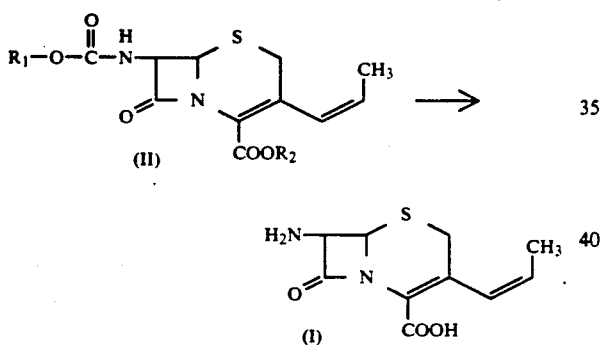

$R_1$ and $R_2$ in the general formula (I) represent alkyl, aryl and aralkyl radicals and may be identical or different.

The process currently in use for the preparation of (I) (see DE 3,613,365 A1) starts from compounds such as those of the formula (III), whose conversion to (I) is carried out in two separate steps.

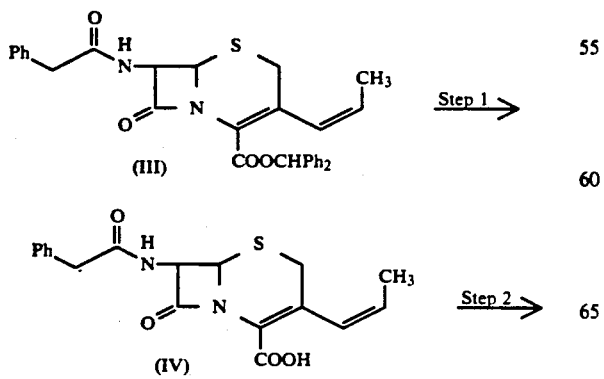

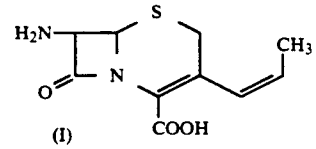

In the course of this, the compound of the formula (III) is converted into the compound (IV) in the first step by treating with a strong acid such as trifluoroacetic acid. The isolated compound (IV) is then converted into the compound (I) in the second step by an enzymatic reaction.

Another, also two-step, process for the preparation of the compound (I) also starts from compounds such as those of the formula (III).

In this case, the compound (V) is prepared in the first step by treating with, for example, phosphorus pentachloride and isolated. Compound (V) can then be converted into the compound (I) by treating with strong acids such as trifluoroacetic acid.

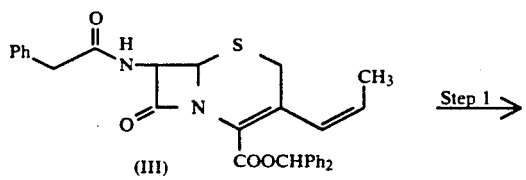

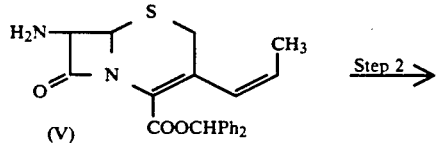

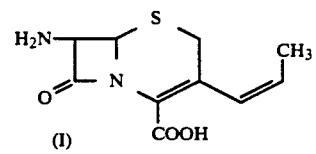

In the processes described in the present invention, however, the compounds of the general formula (II) are converted into the compound (I) in a single synthesis step without isolation of possibly occurring intermediates.

This conversion is carried out by treating the compound (II) with strong protonic acids or by treating with Lewis acids.

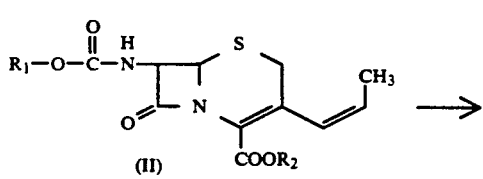

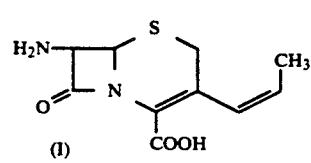

$R_1$ and $R_2$ represent straight-chain or branched $C_1$–$C_{10}$, preferably $C_4$–$C_8$-alkyl or $C_6$–$C_{12}$-aryl, or $C_6$–$C_{12}$-Ar-$C_1$–$C_4$-alkyl radicals.

Preferred examples of the groups represented by $R_1$ and $R_2$ are tert.-butyl, 1,1-dimethylpropyl, 1,1-diethylpropyl, 1,1-dimethylbutyl, 1,1,2,2-tetramethylpropyl, benzyl, 4-methylbenzyl, 4-methoxybenzyl, 2,4-dimethylbenzyl, 3,4-dimethoxybenzyl, 3,4,5-trimethoxybenzyl, diphenylmethyl, dimethylphenylmethyl and di(4-methylphenyl)methyl groups. At the same time, $R_1$ and $R_2$ may be identical or different.

Examples of strong protonic acids are lower alkylcarboxylic acids, formic acid, lower halogenated alkylcarboxylic acids, arylcarboxylic acids, lower alkylsulphonic acids, lower halogenated alkylsulphonic acids and arylsulphonic acids. Preferred examples are acetic acid, formic acid, trifluoroacetic acid, trichloroacetic acid, 4-nitrobenzoic acid, 2,4-dinitrobenzoic acid, methanesulphonic acid, trifluoromethanesulphonic acid, toluenesulphonic acid and 4-nitrobenzenesulphonic acid.

Examples of Lewis acids are aluminium halides, boron halides, titanium halides, tin halides, silyl halides and trialkylsilyl halides.

Preferred examples are aluminium trichloride, boron trifluoride, boron trichloride, boron tribromide, titanium tetrachloride, tin tetrachloride, silicon tetrachloride, trimethylsilyl chloride, trimethylsilyl bromide and trimethylsilyl iodide.

The acid can be employed in equivalent amounts or in a large excess. Liquid acids, such as, for example, trifluoroacetic acid can also be used as solvents.

The reaction can be carried out in the presence of nucleophilic compounds. Nucleophilic compounds which can be used are, for example, arylthiols, heteroarylthiols, aryl alkyl thioethers, trialkylsilanes, triarylsilanes and trialkyltin hydrides. Preferred examples are thioanisole, thiophenol, mercaptobenzothiazole, triethylsilane, triphenylsilane and tributyltin hydride. These nucleophilic compounds can be used in equivalent amounts or in an excess. Particularly preferably, 1 to 4 equivalents of nucleophilic compound are used.

Examples of the solvents which can be used in this invention are halogenated lower hydrocarbons, lower carboxylic acids, lower halogenated carboxylic acids, aromatic hydrocarbons, lower alkyl ethers, cyclic ethers; esters of lower carboxylic acids and lower alkyl nitriles. Preferred examples are dichloromethane, chloroform, formic acid, acetic acid, benzene, toluene, chlorobenzene, diethyl ether, tetrahydrofuran, dioxane, ethyl acetate, butyl acetate and acetonitrile. The reaction temperature is between −40° C. and +30° C. The reaction can be carried out under an inert gas such as, for example, nitrogen, at normal pressure or at elevated pressure.

In this invention, a process is additionally described in which the compounds of the general formula (II) are prepared from compounds of the general formula (VI)

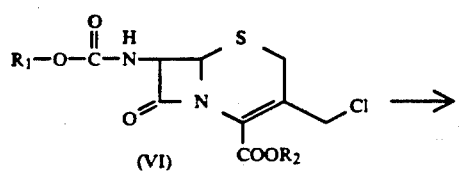

(VI)

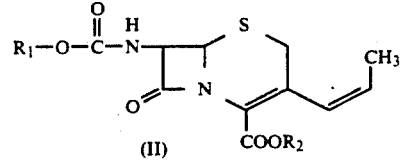

(II)

in which $R_1$ and $R_2$ can have the abovementioned meaning.

In this connection, the compounds (VI) are first treated with triphenylphosphine and alkali metal iodides and then with acetaldehyde and a base.

Triphenylphosphine is added in amounts of 1 to 2 equivalents. Preferred alkali metal iodides are sodium iodide and potassium iodide. The alkali metal iodides are employed in amounts of 0.1 to 2 equivalents. The acetaldehyde is added in amounts of 5 to 50 equivalents, preferably 10 to 20 equivalents are employed.

Bases which can be used in this process are alkali metal hydroxides, alkaline earth metal hydroxides, alkali metal carbonates, alkali metal hydrogencarbonates and alkali metal acetates. Preferred examples are sodium hydroxide, potassium hydroxide, calcium hydroxide, sodium carbonate, potassium carbonate, sodium hydrogencarbonate and sodium acetate.

Suitable solvents for this process are halogenated lower hydrocarbons, aromatic hydrocarbons, lower alkyl ethers, cyclic ethers, esters of lower carboxylic acids, lower alkyl ketones, lower alcohols, carboxylic acid amides and alkyl nitriles.

Particularly preferred examples are dichloromethane, chloroform, 1,2-dichloroethane, toluene, chlorobenzene, diethyl ether, diisopropyl ether, tert.-butyl methyl ether, tetrahydrofuran, dioxane, ethyl acetate, butyl acetate, methanol, ethanol, isopropanol, n-butanol, acetamide, dimethylformamide and acetonirile. Mixtures of these solvents with one another or with water can also be used.

The reaction temperature can be between −5° C. and +70° C.

The reaction can be carried out at normal pressure, but also at elevated pressure.

The invention additionally relates to a process for the preparation of the compounds of the general formula (VI) from the compounds of the general formula (VII), in which $R_1$ and $R_2$ can have the abovementioned meanings.

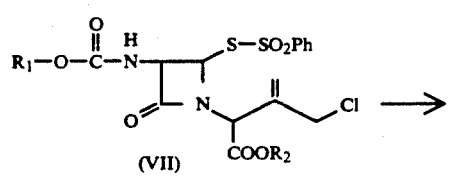

(VII)

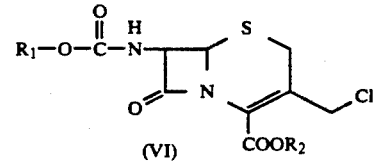

(VI)

In this case, the compounds (VII) are treated at low temperature with a base in a polar solvent.

Suitable polar solvents for this process are carboxylic acid amides and cyclic urea derivatives. Particularly preferred examples are dimethylformamide, dimethylacetamide, acetamide, 1,3-dimethyl-2-imidazolidinone, 1,3-dimethyltetrahydro-2(1H)-pyrimidinone or mixtures of these solvents. Mixtures of these solvents with water are also possible.

Bases suitable for this process are ammonia, alkylamines, alkali metal hydroxides, alkali metal carbonates, alkali metal hydrogencarbonates and alkali metal fluorides. Ammonia, methylamine, ethylamine, triethylamine, diisopropylamine, sodium hydroxide, potassium hydroxide, sodium carbonate, potassium carbonate and sodium hydrogencarbonate are particularly preferred.

These bases can be employed in equivalent amounts, but also in an excess. 1 to 4 equivalents of base are particularly preferably used.

The reaction temperature can be between $-70°$ C. and $0°$ C, the reaction being preferably carried out between $-50°$ C. and $-10°$ C.

A process for the preparation of the compounds (VII) from the compounds of the general formula (VIII) is furthermore described, in which $R_1$ and $R_2$ have the above-mentioned meanings.

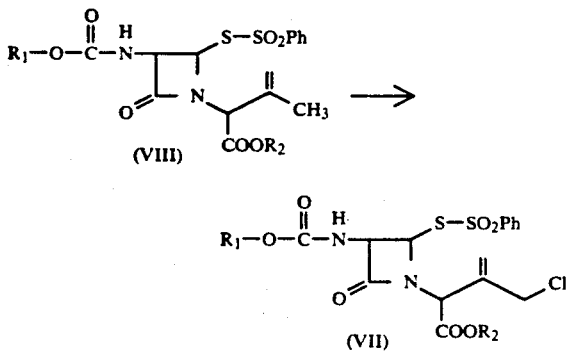

In this process, the compounds (VIII) are treated with a chlorinating agent in an organic solvent.

Suitable solvents for this process are halogenated lower hydrocarbons, aromatic hydrocarbons, lower alkyl ethers, cyclic ethers, esters of lower carboxylic acids and lower carboxylic acid amides.

Particularly preferred examples are dichloromethane, chloroform, carbon tetrachloride, toluene, chlorobenzene, diethyl ether, tert.-butyl methyl ether, tetrahydrofuran, dioxane, ethyl acetate, butyl acetate and dimethylformamide. These solvents can also be used in a mixture with water.

Suitable chlorinating agents for this purpose are chlorine, alkyl hypochlorite, hypochlorous acid, chlorine dioxide and sulphuryl chloride. Particularly preferred examples are chlorine, tert.-butyl hypochlorite, chlorine dioxide, hypochlorous acid and sulphuryl chloride.

The chlorinating agent can be used in equivalent amounts or in an excess. In general, the reaction is carried out with 1 to 2 equivalents of chlorinating agent. The reaction temperature can be between $-40°$ C. and $+40°$ C., the reaction being particularly preferably carried out between $-30°$ C. and $+20°$ C.

Finally, a process for the preparation of the compounds (VIII) from compounds with the general formula (IX) is described in this invention

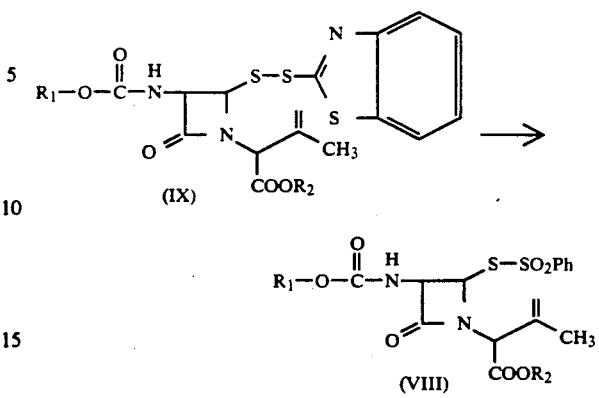

in which $R_1$ and $R_2$ have the abovementioned meaning.

In this process, the compounds (IX) are converted into the compounds (VIII) by treating with benzenesulphinic acid, if appropriate in the presence of an oxidizing agent.

Suitable solvents for this process are lower alkyl alcohols, aromatic hydrocarbons, halogenated lower hydrocarbons, esters of lower carboxylic acids and lower alkyl ethers. Particularly preferred examples are methanol, ethanol, isopropanol, benzene, toluene, xylene, chlorobenzene, ethyl acetate, butyl acetate, dichloromethane, chloroform, diethyl ether, tert.-butyl methyl ether and diisopropyl ether. Mixtures of these solvents with one another or with water are also possible.

The benzenesulphinic acid used in this process can be used in an equivalent amount or in an excess. The reaction is particularly preferably carried out with 1 to 4 equivalents. The benzenesulphinic acid can also be generated in situ from sodium benzenesulphinate by addition of strong acids such as, for example, hydrochloric acid or sulphuric acid.

The oxidizing agents optionally used in this process are, for example, hydrogen peroxide, chloramine T, chloramine B, bleaching powder liquor, calcium hypochlorite, lithium hypochlorite, sodium hypochlorite, N-chlorosuccinimide and chlorine. Hydrogen peroxide is particularly preferred as the oxidizing agent.

The reaction temperature can be between $0°$ C. and $30°$ C.

When using an oxidizing agent, catalysts such as alkali metal iodides can also be used advantageously.

The synthesis of the compounds of the general formula (IX) is carried out analogously to A. I. Scott, R. Shankaranarayan, Tetrahedron Letters 29, 3179-3182 (1988).

EXAMPLE 1

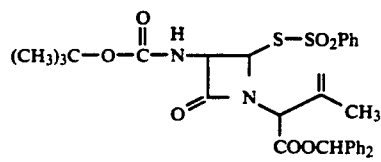

Diphenylmethyl 2-[4-(benzenesulphonylthio)-3-tert.-butyloxycarbonylamino-2-oxo-azetidin-1-yl]-3-methylenebutyrate

A. Synthesis of the starting material

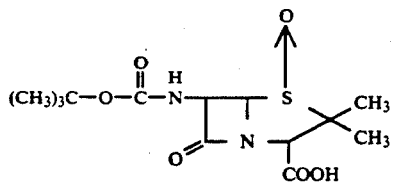

A.1.

6-tert.-Butyloxycarbonylamino-penicillanic acid-1-oxide 216 g (1 mol) of 6-aminopenicillanic acid are suspended in 2000 ml of ethanol and 200 ml of water. 140 ml (1 mol) of triethylamine are then added, the mixture is stirred for 15 min. and 240 g (1.11 mol) of ditert.-butyl pyrocarbonate are added to the clear solution. The reaction mixture is stirred at 20° C. for 1 h, then concentrated on a rotary evaporator in vacuo to about 1000 ml volume. 1500 ml of water are added to the residue and after adding 87 g of sodium hydrogencarbonate the mixture is extracted with 500 ml of ethyl acetate. The organic phase is separated off, and the aqueous phase is covered with 1500 ml of ethyl acetate and brought to pH=3 with 2N sulphuric acid. The organic phase is separated off, and the aqueous phase is extracted twice more with 500 ml portions of ethyl acetate. The combined organic phases are evaporated in vacuo, and the resulting oily residue is dissolved in a solution of 87 g of sodium hydrogencarbonate in 2000 ml of water. After adding 4 g of sodium tungstate dihydrate 110 ml of 30% hydrogen peroxide are added dropwise at 15 to 20° C. in the course of 15 min. The reaction solution is subsequently stirred at 15° to 20° C. for 1.5 h, then covered with 1000 ml of ethyl acetate and brought to pH=3 with 2N sulphuric acid. The precipitate which deposits in the course of this is filtered off with suction, washed with 1000 ml of water and a little ethyl acetate and dried in vacuo.

Yield: 201 g of product=60.5% of theory.
NMR (250 MHz, CDCl$_3$): 1.2[3]s, 1.4[9]s, 1.6[3]s, 4.35[1]s, 5.45[1]d J=5Hz,
5.6[1]dd J=10Hz J=5Hz, 6.2[1]d J=10Hz.

R$_f$ value: 0.33 (Mobile phase: organic phase of a vigorously shaken mixture of 300 ml of butyl acetate, 36 ml of n-butanol, 100 ml of glacial acetic acid and 60 ml of pH 7 buffer solution).

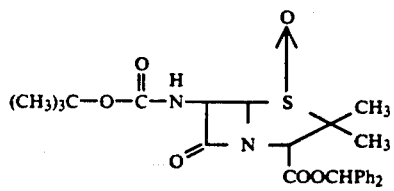

A.2.

Diphenylmethyl 6-tert.-butyloxycarbonylamino-penicillanate-1-oxide 132.8 g (0.4 mol) of 6-tert.-butyloxycarbonylamino-penicillanic acid-1-oxide are suspended in 400 ml of toluene and 520 ml of a 0.8 molar solution of diphenyl-diazomethane in toluene are added. The reaction solution is stirred at 20° C. overnight and 1000 ml of diisopropyl ether are then added. The mixture is stirred at 10° C. for 1 h, and the precipitate is filtered off with suction, washed with 500 ml of diisopropyl ether and dried in vacuo.

Yield: 166.9 g of product=83.7% of theory.
NMR (250 MHz, CDCl$_3$): 0.9[3]s, 1.45[9]s, 1.7[3]s, 4.75[1]s, 5.0[1]d J=5Hz, 5.7[1]dd J=10Hz J=5Hz, 6.05[1]d J=10Hz, 7.0[1]s, 7.3-7.45[10]m R$_f$ value: 0.55 (Toluene/ethyl acetate 8:2)

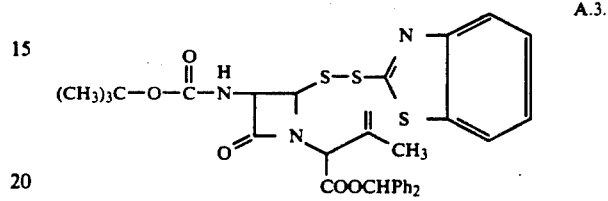

A.3.

Diphenylmethyl 2-4-(benzothiazol-2-yldithio)-3-tert.-butyloxycarbonylamino-2-oxo-azetidin-1-yl]-3-methylenebutyrate 60 g (0.12 mol) of diphenylmethyl 6-tert.-butyloxycarbonylamino-penicillanate-1-oxide are heated under reflux in a water separator for 1.5 h together with 20.4 g (0.12 mol) of 2-mercaptobenzothiazole in 850 ml of toluene. After cooling, the reaction solution is evaporated in vacuo. The oily residue is stirred overnight in 400 ml of diisopropyl ether. The crystalline precipitate formed is filtered off with suction and washed with diisopropyl ether. This crude product is heated to reflux in 500 ml of diisopropyl ether and brought into solution at reflux temperature with 60 ml of ethyl acetate. The hot solution is filtered and slowly cooled. The precipitated product is filtered off with suction, washed with diisopropyl ether and dried in vacuo.

Yield: 40.8 g of product=52% of theory.
NMR (250 MHz, CDCl$_3$): 1.45[9]s, 1.9[3]s, 4.95[1]s, 5.05[1]s, 5.15[1]s, 5.3[1]dd J=10 Hz J=5Hz, 5.5[1]d J=5Hz, 5.55[1]d J=10Hz, 6.9[1]s, 7.2-7.35[11]m, 7.45[1]ddd J=7Hz J=2Hz, 7.75[1]dd J=7Hz J=2Hz, 7.9[1]dd J=7Hz J=2Hz R$_f$ value: 0.6 (Toluene/ethyl acetate 8:2).

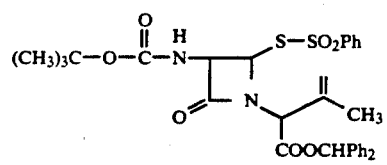

B.

Diphenylmethyl 2-4-(benzenesulphonylthio)-3-tert.-butyloxycarbonylamino-2-oxo-azetidin-1-yl]-3-methylenebutyrate 62.5 9 (0.1 mol) of diphenylmethyl 2-[4-benzothiazol-2-yldithio)-3-tert.-butyloxycarbonylamino-2-oxoazetidin-1-yl]-3-methylenebutyrate are suspended in 250 ml of toluene and 250 ml of saturated sodium chloride solution are added. 32.8 g (0.2 mol) of sodium benzenesulphinate and 40 ml of 6N hydrochloric acid are then added, the mixture is stirred at 20° C. for 2.5 h and the precipitate formed is filtered off with suction. The phases in the filtrate are separated and 7 ml of 30% hydrogen peroxide are added to the organic phase. The reaction mixture is stirred at 20° C. overnight and evaporated in vacuo, and the residue is thoroughly stirred in 700 ml of diisopropyl ether. The crystalline precipitate formed is filtered off with suction, washed with diisopropyl ether and dried in vacuo.

Yield: 32 g of product=51.4% of theory.

NMR (250 MHz, CDCl₃): 1.4[9]s, 1.75[3]s, 4.4[1]s, 4.75[1]s, 4.85[1]s, 5.0[2]m, 5.75[1]d J=5Hz, 6.85[1]s, 7.3-7.6[13]m, 7.8[2]d J=7Hz.

R$_f$ value: 0.5 (Toluene/ethyl acetate 8:2).

EXAMPLE 2

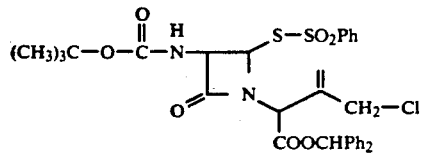

Diphenylmethyl 2-4-(benzenesulphonylthio)-3-tert.-butyloxocarbonylamino-2-oxo-azetidin-1-yl]-4-chloro -3-methylenebutyrate 3.6 g (0.05 mol) of chlorine gas are passed into a solution of 19.1 g (0.03 mol) of diphenylmethyl 2-[4-(benzenesulphonylthio)-3-tert.-butyloxycarbonylamino-2-oxo-azetidin-1-yl]-3-methylenebutyrate in 300 ml of ethyl acetate at 0° to −2° C. in the course of 5 min. The reaction mixture is subsequently stirred at 0° C. for 1.5 h, then washed with 300 ml of saturated sodium hydrogencarbonate solution and 300 ml of water. The ethyl acetate phase is dried using sodium sulphate and evaporated in vacuo. The residue is thoroughly stirred in 100 ml of isopropanol, and the crystalline precipitate formed is filtered off with suction, washed with isopropanol and dried in vacuo.

Yield: 13.5 g of product=67.1% of theory.

NMR (250 MHz, CDCl₃): 1.4[9]s, 4.05[1]d J=14Hz, 4.15[1]d J=14Hz, 4.55[1]s, 4.95[2]m, 5.15[1]s, 5.2[1]s, 5.8[1]d J=5Hz, 6.85[1]s, 7.25-7.55[13]m, 7.8[2]d J=7Hz

R$_f$ value: 0.54

EXAMPLE 3

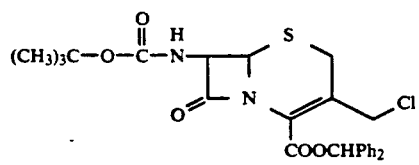

Diphenylmethyl 7-tert.-butyloxycarbonylamino-3-chloromethyl-3-cephem-4-carboxylate A solution of 13.5 g (0.02 mol) of diphenylmethyl 2-[4-(benzenesulphonylthio)-3-tert.-butyloxycarbonylamino-2-oxo-azetidin-1-yl]-4-chloro-3-methylenebutyrate in 50 ml of DMF is added dropwise at −40° C. to a solution of 0.63 g (0.037 mol) of ammonia gas in 35 ml of DMF. The reaction mixture is subsequently stirred at −40° C. to −50° C. for 1 h, 14 ml of IN hydrochloric acid are added dropwise at −40° C. and the mixture is diluted with 600 ml of water. The precipitate formed is washed with water and thoroughly stirred in 50 ml of methanol. The crystal suspension is filtered off with suction, washed with methanol and dried in vacuo.

Yield: 9.5 g of product=92% of theory

NMR (300 MHz, CDCl₃): 1.45[9]s, 3.5[1]d J 16Hz, 3.65[1]d J=16Hz, 4.35[1]d J=13Hz, 4.45[1]d J=13Hz, 5.0[1]d J =5Hz, 5.25[1]d J=10Hz, 5.65[1]dd J=10Hz J=5Hz, 6.95(1)s, 7.25-7.5[10]m

R$_f$ value: 0.72 (Toluene/ethyl acetate 8:2)

EXAMPLE 4

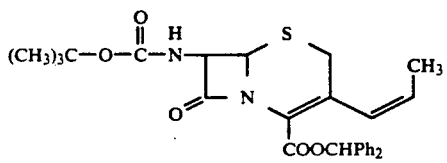

Diphenylmethyl 7-tert.-butyloxycarbonylamino-3-(propen-1-yl)-3-cephem-4-carboxylate 2.57 g (5 mmol) of diphenylmethyl 7-tert.-butyloxycarbonylamino-3-chloromethyl-3-cephem-4-carboxylate are dissolved in 20 ml of dichloromethane and 20 ml of isopropanol. After adding 0.84 g (5 mmol) of potassium iodide and 1.31 g (5 mmol) of triphenylphosphine, the mixture is stirred at 20° C. for 4 h. 4.4 g (100 mmol) of acetaldehyde and a solution of 0.69 g (5 mmol) of potassium carbonate in 15 ml of water are then added and the reaction mixture is stirred vigorously at 20° C. for 30 min. The organic phase is separated off, dried using magnesium sulphate and evaporated in vacuo. The residue is purified by chromatography on 300 g of silica gel Si60 0.04 to 0.063 mm using a toluene-ethyl acetate 9:1 mixture as the eluent. After evaporating the appropriate fractions in vacuo, the product is isolated as a solid foam.

Yield: 1 g of product (mixture of the Z- and E-isomers in the ratio 1:8)=39.5% of theory.

NMR (250 MHz, DMSO-d₆): 1.35-1.4[12]m, 3.55(2)s, 5.2[1]d J=5Hz, 4.9-5.1[2]m, 6.1[1]d J =12Hz, 6.85[1]s, 7.2-7.5[10]m, 8.0[1]d J=10Hz The NMR data apply to the Z-isomer.

R$_f$ value: 0.71 for the Z-isomer (toluene/ethyl acetate 8:2)=0.73 for the E-isomer (toluene/ethyl acetate 8:2).

EXAMPLE 5

7-APCA

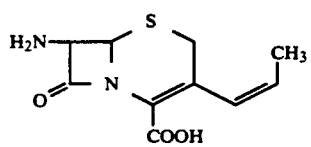

(7-Amino-3-(propen-1-yl)-3-cephem-4-carboxylic acid)

5 g (10.85 mmol) of diphenylmethyl 7-tert.-butyloxycarbonylamino-3-(propen-1-yl)-3-cephemcarboxylate are stirred in 50 ml of trifluoroacetic acid at 20° C. for 3 h. 300 ml of diisopropyl ether are then added dropwise with ice-cooling and the mixture is subsequently stirred for 15 min. The precipitate which deposits is filtered off with suction, washed with diisopropyl ether and suspended in 50 ml of water. This aqueous suspension is brought to pH=8.3 with about 3 ml of 25% ammonia water. 2 g of active carbon are added to the aqueous suspension and the mixture is filtered. The filtrate is brought to pH=2.5 with about 2 ml of 6N hydrochloric acid. The precipitate formed is filtered off with suction, washed with water and acetone and dried in vacuo.

Yield: 2.0 g of product=76.9% of theory.

NMR (200 MHz, DCOOD): 1.8[3]dd J 7.5Hz J 2Hz, 3.65[2]q J=15Hz, 5.4[1]d J=5Hz, 5.5[1]d J=5Hz, 5.95[1]dq J=12Hz J=7.5Hz, 61.5[1]dd J=12Hz J=2Hz. The NMR data apply to the Z-isomer.

R$_f$ value: 0.5 for the Z-isomer (n-propanol-ethyl acetate-water 16:12:12) 0.52 for the E-isomer (n-propanol-ethyl acetate-water 16:12:12)

EXAMPLE 6

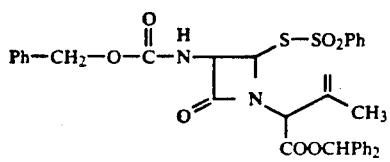

Diphenylmethyl
2-[4-(benzenesulphonylthio)-3-benzyloxycarbonylamino-2-oxo-azetidin-2-yl1-3-methylenebutyrate A. Synthesis of the starting material

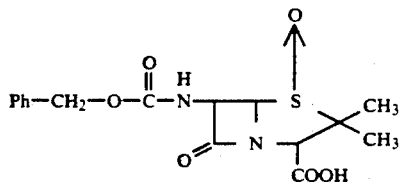

A.1.

6-Benzyloxycarbonylamino-penicillanic acid-1-oxide 108 g (0.5 mol) of 6-aminopenicillanic acid are dissolved in 1500 ml of water together with 185 g (2.2 mol) of sodium hydrogencarbonate. A solution of 81 ml (0.54 mol) of benzyloxycarbonyl chloride in 300 ml of diethyl ether is then added dropwise at 20° C. with vigorous stirring in the course of 15 min. After completion of the dropwise addition, 10 g (0.095 mol) of sodium hydrogencarbonate dissolved in 250 ml of water are added once more and the mixture is subsequently stirred at 20° C. for 2 h. It is then extracted three times with 300 ml portions of diethyl ether, and the aqueous phase is covered with 500 ml of ethyl acetate and brought to pH=4 with 2N sulphuric acid while stirring vigorously. The aqueous phase is extracted twice more with 1000 ml portions of ethyl acetate, and the combined organic phases are dried using magnesium sulphate and evaporated in vacuo. 165.2 g of solid white foam are thus obtained, which is dissolved in 2000 ml of water and 450 ml of ethanol together with 40.1 g (0.48 mol) of sodium hydrogencarbonate. 3.6 g (0.011 mol) of sodium tungstate dihydrate are then added at 0° C. and 50 ml (0.49 mol) of 30% hydrogen peroxide are added dropwise. The reaction mixture is subsequently stirred at 0° C. for 2 h, then brought to pH=3 with 2N sulphuric acid and extracted twice with 2000 ml portions of ethyl acetate. The combined organic phases are dried with magnesium sulphate and evaporated to dryness in vacuo.

Yield: 152.9 g of product=83.5% of theory.

NMR (250 MHz, CDCl$_3$): 1.25[3]s, 1.7[3]s, 4.15[1]s, 5.0[1]d J 5Hz, 5.15[2]s, 5.75[1]dd J 10Hz J 5Hz, 6.45[1]d J 10Hz, 7.3[5]s, 7.65[1]s broad R$_f$ value: 0.44 (Mobile phase: organic phase of a vigorously shaken mixture of 300 ml of butyl acetate, 36 ml of n-butanol, 100 ml of glacial acetic acid and 60 ml of pH 7 buffer solution).

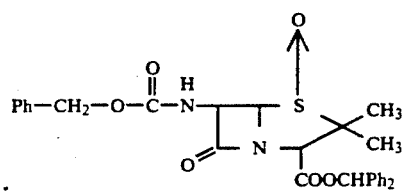

A.2.

Diphenylmethyl
6-benzyloxycarbonylamino-penicillanate-1-oxide 53.2 g (0.145 mol) of 6-benzyloxycarbonylaminopenicillanic acid-1-oxide are dissolved in 200 ml of ethyl acetate. 250 ml of a 0.6 molar solution of diphenyldiazomethane in toluene are added dropwise to this solution at 10° C. The reaction solution is stirred at 20° C. overnight and then evaporated in vacuo. The oily residue is chromatographed on 1.2 kg of silica gel Si60 0.04 to 0.063 mm using a toluene-ethyl acetate 8:2 mixture as the eluent. After evaporating the appropriate fractions in vacuo, the product is obtained as a solid white foam.

Yield: 33.4 g of product=43.2% of theory

NMR (250 MHz, CDCl$_3$): 1.35[3]s, 1.65[3]s, 4.75[1]s, 4.9[1]d J=5Hz, 5.1[2]s, 5.75[1]dd J=10Hz J=5Hz, 6.4[1]d J=10Hz, 6.95[1]s, 7.1-7.4[15]m

R$_f$ value: 0.55 (Toluene/ethyl acetate 8:2)

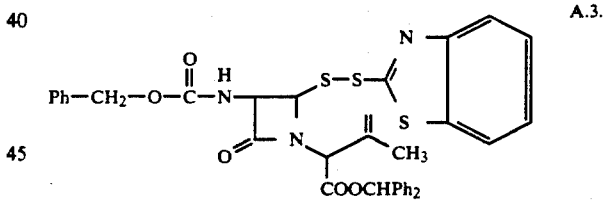

A.3.

Diphenylmethyl
2-[4-(benzothiazol-2-yldithio)-3-benzyloxycarbonylamino-2-oxo-azetidin-1-yl-3-methylenebutyrate 39.8 g (74.7 mmol) of diphenylmethyl 6-benzyloxycarbonylamino-penicillanate-1-oxide are heated under reflux in a water separator for 1.5 h together with 12.48 g (74.7 mmol) of 2-mercaptobenzothiazole in 450 ml of toluene. The reaction solution is then evaporated in vacuo and the residue is chromatographed on 1500 g of silica gel Si60 0.04 to 0.063 mm using a toluene-ethyl acetate 8:2 mixture as the eluent. The appropriate fractions are evaporated in vacuo and yield the product as a solid white foam.

Yield: 31.5 g of product=62% of theory.

NMR (250 MHz, CDCl$_3$): 1.9[3]s, 4.95[1]s, 5.0-5.1[2]m, 5.15-5.25[2]m, 5.35[1]dd J=10Hz J=5Hz, 5.55[1]d J=5Hz, 6.35[1]d J=10Hz, 6.9[1]s, 7.1-7.4[17]m, 7.65-7.8[2]m

R$_f$ value: 0.54 (Toluene/ethyl acetate 8:2).

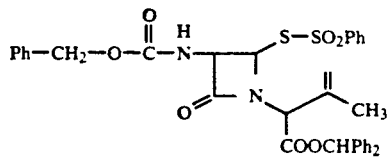

Diphenylmethyl 2-[4-(benzenesulphonylthio)-3-benzyloxycarbonylamino-2-oxo-azetidin-2-yl]-3-methylenebutyrate 10.1 g (60 mmol) of sodium benzenesulphinate 60 ml of saturated sodium chloride solution and 6 ml of 6N hydrochloric acid are added successively at 20° C. to 20.4 g (30 mmol) of diphenylmethyl 2-[4-(benzothiazol-2-yldithio)-3-benzyloxycarbonylamino-2-oxo-azetidin-1-yl]-3-methylenebutyrate in 80 ml of toluene. The reaction mixture is stirred vigorously for 10 min. The precipitate which deposits is filtered off with suction, and the organic phase in the filtrate is separated off. 30 mg of potassium iodide and 2.1 ml (21 mmol) of 30% hydrogen peroxide are then added to the organic phase and the mixture is stirred at 20° C. for 30 min. It is then dried with magnesium sulphate and evaporated in vacuo. The oily residue is chromatographed on 700 g of silica gel Si60 0.04 to 0.063 mm using a petroleum ether-ethyl acetate 7:3 mixture as the eluent. The appropriate fractions are evaporated in vacuo and yield the product as a solid white foam.

Yield: 16.5 g of product=83.7% of theory.

NMR (250 MHz, CDCl₃): 1.75[3]s, 4.4[1]s, 4.8[1]s, 4.9[1]s, 5.0–5.15[3]m, 5.35[1]d J=10Hz, 5.85[1]d J 5Hz, 6.85[1]s, 7.2–7.55[18]m, 7.8[2]d J=7Hz

R$_f$ value: 0.25 (Petroleum ether/ethyl acetate 7:3)

EXAMPLE 7

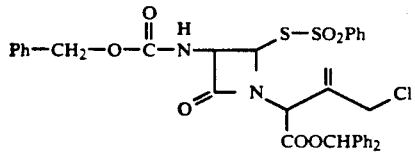

Diphenylmethyl 2-[4-(benzenesulphonylthio)-3-benzyloxycarbonylamino-2-oxo-azetidin-1-yl]-4-chloro-3-methylenebutyrate 7.9 g (12 mmol) of diphenylmethyl 2-[4-(benzenesulphonylthio)-3-benzyloxycarbonylamino-2-oxo-azetidin-2-yl]-3-methylenebutyrate are dissolved in 150 ml of ethyl acetate. 1.3 g (18 mmol) of chlorine gas are then passed in at 0° to 5° C. in the course of 10 min. The reaction solution is subsequently stirred at 20° C. for 2 h and then evaporated in vacuo. The residue is chromatographed on 100 g of HD-SIL 18-30-60 0.02 to 0.045 mm (Kronwald Separationstechnik GmbH) using an acetonitrile-water 65:35 mixture as the eluent. After evaporating the appropriate fractions in vacuo, the product is obtained as a solid foam.

Yield: 4.23 g of product=51% of theory.

NMR (250 MHz, CDCl₃): 4.0[1]d J 12Hz, 4.15[1]d J 12Hz, 4.5[1]s, 4.9–5.10[4]m, 5.6[1]d J=10Hz, 5.85[1]d J=5Hz, 6.85[1]s, 7.2–7.45[18]m, 7.75[2]d J=7Hz

R$_f$ value: 0.52 (Toluene/ethyl acetate 8:2)

EXAMPLE 8

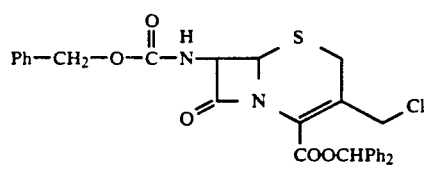

Diphenylmethyl 7-benzyloxycarbonylamino-3-chloromethyl3-cephem-4-carboxylate

A solution of 3.75 g (5 mmol) of diphenylmethyl 2-[4-(benzenesulphonylthio)-3-benzyloxycarbonylamino-2-oxo-azetidin-1-yl]-4-chloro-3-methylenebutyrate in 16 ml of DMF is added dropwise at -40° C. to a solution of 0.21 g (12.5 mmol) of ammonia gas in 25 ml of DMF. After stirring at −40° C. for 20 min, 6 ml of 1N hydrochloric acid are water, the precipitate formed is filtered off with suction and washed with water. After drying in vacuo, the precipitate is thoroughly stirred in 30 ml of diisopropyl ether, filtered off with suction again and dried in vacuo.

Yield: 1.9 g of product=69% of theory.

NMR (300 MHz, CDCl₃): 3.45[1]d J 16Hz, 3.6[1]d J 16Hz, 4.35[1]d J=12Hz, 4.45[1]d J 12Hz, 4.95[1]d J 5Hz, 5.15[2]s, 5.6[1]d J 10Hz, 5.7[1]dd J=10Hz J=5Hz, 7.0[1]s, 7.2–7.5[15]m

R$_f$ value: 0.68 (Toluene/ethyl acetate 8:2)

EXAMPLE 9

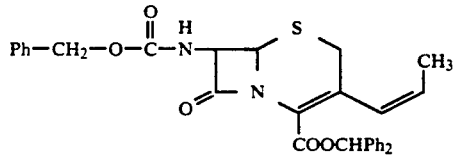

Diphenylmethyl 7-benzyloxycarbonylamino-3-(propen-1-yl)-3-cephem-4-carboxylate 0.33 g (2 mmol) of potassium iodide and 0.52 g (2 mmol) of triphenylphosphine are added to 1.1 g (2 mmol) of diphenylmethyl 7-benzyloxycarbonylamino-3-chloromethyl-3-cephem-4-carboxylate in 10 ml of dichloromethane and 10 ml of sopropanol. The reaction mixture is stirred vigorously at 20° C. for 4 h and 1.8 g (40 mmol) of acetaldehyde and 0.28 g (2 mmol) of potassium carbonate in 10 ml of water are then added. The reaction mixture is stirred vigorously for 30 min., the phases are then separated and the organic phase is dried using magnesium sulphate. The oil obtained after evaporating in vacuo is chromatographed on 120 g of silica gel Si60 0.04 to 0.063 mm using a toluene-ethyl acetate 9:1 mixture as the eluent. After evaporating the suitable fractions in vacuo, the product is obtained as a solid foam.

Yield: 0.45 g of product=41% of theory (Mixture of the E- and Z-isomers in the ratio 1:9).

NMR (200 MHz, DMSO-d₆): 1.4[3]d J 7Hz, 3.55[2]s, 5 1[2]s, 5.2[1]d J=5Hz, 5.4–5.65[2]s, 6.1[1]d J 10Hz, 6.9[1]s, 7.2–7.55[15]m, 8.5[1]d J=10Hz The NMR data apply to the Z-isomer.

R_f value: 0.63 for the Z-isomer (toluene/ethyl acetate 8:2) 0.69 for the E-isomer (toluene/ethyl acetate 8:2).

EXAMPLE 10

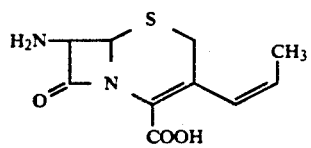

(7-Amino-3-(propen-1-yl)-3-cephem-4-carboxylic acid)

Method A 0.8 g (4 mmol) of trimethylsilyl iodide is added to 0.55 g (1 mmol) of diphenylmethyl 7-benzyloxycarbonylamino-3-(propen-1-yl)-3-cephem-4-carboxylate in 5 ml of dichloromethane under nitrogen and the mixture is stirred at 20° C. for 2 h. The reaction solution is then extracted with 50 ml of 2N sulphuric acid and the aqueous phase is brought to pH=3.5 with 25% aqueous ammonia. The precipitate which deposits is filtered off with suction, washed with water and acetone and dried in vacuo.

Yield: 0.13 9 of product=55% of theory.

Method B 1 1 g (2 mmol) of diphenylmethyl 7-benzyloxycarbonylamino-3-(propen-1-yl)-3-cephem-4-carboxylate are dissolved in 10 ml of trifluoroacetic acid and 0.93 g (8 mmol) of triethylsilane is added. After stirring at 20° C. for 2 h, 60 ml of diisopropyl ether are added dropwise with ice-cooling and the mixture is subsequently stirred for 20 minutes. The precipitate which deposits is filtered off with suction, washed with diisopropyl ether and suspended in 20 ml of water. This aqueous suspension is brought to pH=8.3 with about 1 ml of 25% ammonia water. 1 g of active carbon is added to the aqueous suspension and the mixture is filtered. The filtrate is brought to pH=2.5 with about 0.5 ml of 6N hydrochloric acid. The precipitate formed is filtered off with suction, washed with water and acetone and dried in vacuo.

Yield: 0.091 g of product=19% of theory.

Method C 13.7 g=9.25 ml (120 mmol) of trifluoroacetic acid are added dropwise at 0° C. to a solution of 5 g (40 mmol) of boron tribromide in 40 ml of dichloromethane. The resulting suspension is evaporated to dryness in vacuo. The residue is dissolved in 40 ml of trifluoroacetic acid and added at −20° C. to a solution of 2.75 g (5 mmol) of diphenylmethyl 7-benzyloxycarbonylamino-3-(propen-1-yl)-3-cephem-4-carboxylate and 2 ml of anisole.

The reaction mixture is stirred at 0° C. for 1 h, then evaporated to dryness in vacuo. The residue is crystallized from diethyl ether, filtered off with suction and suspended in 40 ml of water. The aqueous suspension is brought to pH=0.3 with conc. hydrochloric acid, stirred for 5 min. and then filtered. The filtrate is brought to pH=3.0 with 25% aqueous ammonia while cooling in ice. The precipitate which deposits is filtered off with suction, washed with water and dried in vacuo.

Yield: 0.87 g of product=72.5% of theory.

EXAMPLE 11

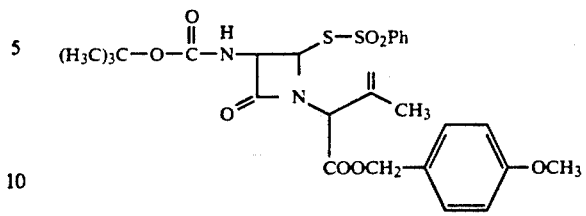

4-Methoxybenzyl 2-[4-(benzenesulphonylthio)-3-tert.-butyloxycarbonylamino-2-oxo-azetidin-1-yl]-3-methylenebutyrate A. Synthesis of the starting material

A.1.

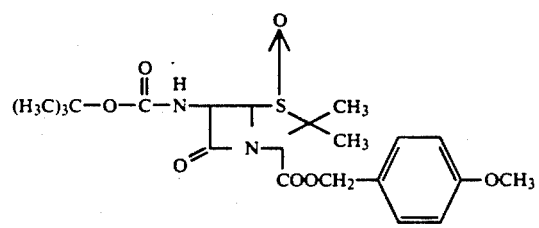

4-Methoxybenzyl 6-tert.-butyloxycarbonylamino-penicillanate 132.9 g (0.4 mol) of 6-tert.-butyloxycarbonylaminopenicillanic acid-1-oxide are dissolved in 400 ml of DMF. 54 ml (0.4 mol) of triethylamine and 93.9 g (0.6 mol) of 4-methoxybenzyl chloride are then added at 5-10° C. After adding 66.4 g (0.4 mol) of potassium iodide, the reaction mixture is stirred at 25° C. for 16 h. 1500 ml of water are then added dropwise to the reaction mixture with vigorous stirring and the mixture is subsequently stirred for 3 h. The precipitate formed is filtered off with suction and dissolved in 1000 ml of acetone at 35° C., and 1000 ml of water are slowly added at 20° C. The mixture is subsequently stirred at 20° C. for 1 h, then the white crystalline precipitate is filtered off with suction, washed with 500 ml of water and 500 ml of water-acetone in the ratio 1:1 and dried in vacuo.

Yield: 136.2 g of product=75.7% of theory

NMR (250 MHz, CDCl₃): 1.05[3]s, 1.45[9]s, 165[3]s, 3 8[3]s, 4.65[1]s, 5.0[1]d J=5Hz, 5.1[1]d J 12Hz, 5.25[1]d J 12Hz, 5.7[1]dd J=10Hz J=5Hz, 6.05[1]d J=10Hz, 6.9[2]d J=8Hz, 7.3[2]d J=8Hz

R_f value: 0.33 (toluene/ethyl acetate 8:2). A.2

A.2

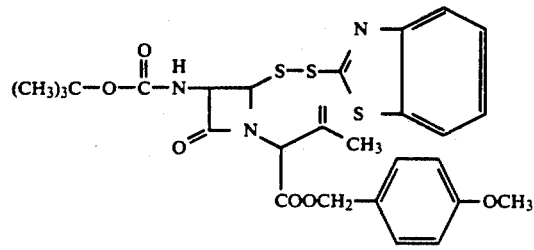

4-Methoxybenzyl 2-[4-(benzothiazol-2-yldithio)-3-tert.-butyloxycarbonylamino-2-oxo-azetidin-1-yl]-3-methylenebutyrate 90.4 g (0.2 mol) of 4-methoxybenzyl 6-tert.-butyloxycarbonylamino-penicillanate are heated under reflux in a water separator for 1 h together with 34.3 g (0.2 mol) of 2-mercaptobenzothiazole in 1600 ml of toluene. The reaction solution is then evaporated to dryness in vacuo. The oily residue is stirred in 500 ml of diisopropyl ether for 16 h. The crystalline precipitate formed is filtered off with suction and dried in vacuo.

Yield: 77.4 g = 64.2% of theory

NMR (300 MHz, CDCl3): 1.5[9]s, 1.9[3]s, 3.8[3]s, 4.95[1]s, 5.0[1]s, 5.15[2]AB quartet, 5.2[1]s, 5.35[1]dd J 10Hz, J=5Hz, 5.5[1]d J=5Hz, 5.65[1]d J=10Hz, 6.85[2]d J=8Hz, 7.25[2]d J=8Hz, 7.35[1]tr J =8Hz, 7.45[1]tr J=8Hz, 7.8[1]d J=8Hz, 7.9[1]d J=8Hz R$_f$ value: 0.43 (toluene/ethyl acetate 8:2) B.

B.

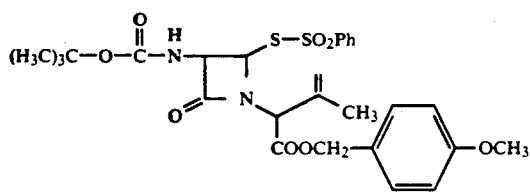

4-Methoxybenzyl 2-[4-(benzenesulohonylthio)-3-tert.-butyloxycarbonylamino-2-oxo-azetidin-1-yl]-3-methylenebutyrate 30 g (0.05 mol) of 4-methoxybenzyl 2-[4-(benzothiazol-2-yldithio)-3-tert. -butyloxycarbonylamino-2-oxo-azetidin-1-yl]-3-methylenebutyrate are dissolved in 100 ml of toluene and 100 ml of saturated sodium chloride solution and 16.4 g (0.1 mol) of sodium benzenesulphinate are added. After adding 17 ml of 6N hydrochloric acid dropwise, the reaction mixture is stirred at 20° C. for 3 h. The precipitate formed is filtered off with suction, the phases in the filtrate are separated and 6 ml of 30% strength hydrogen peroxide are added to the organic phase, which is stirred at 20° C. for 16 h. After drying with sodium sulphate, the reaction solution is evaporated in vacuo, and the resultant oil is stirred in 200 ml of diisopropyl ether for 3 h. The precipitate formed is filtered off with suction and washed with diisopropyl ether. The precipitate is thoroughly stirred in 200 ml of diethyl ether, filtered off with suction, washed with a little diethyl ether and dried in vacuo.

Yield: 14 g of product=48.6% of theory

NMR (250 MHz, CDCl3): 1.4[9]s, 1.75[3]s, 3.85[3]s, 4.55[1]s, 4.75[1]s, 4.85[1]s 5.0-5.2[4]m, 5.75[1]d J=5Hz, 6.9[2]d J=8Hz, 7.3[2]d J=8Hz, 7.45-7.65[3]m, 7.85[2]d J=8Hz

R$_f$ value: 0.32 (toluene/ethyl acetate 8:2)

EXAMPLE 12

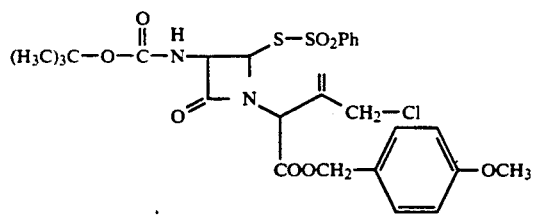

4-Methoxybenzyl 2-[4-(benzenesulphonylthio)3-tert.-butyloxycarbonylamino-2-oxo-azetidin-1-yl]-4-chloro-3-methylenebutyrate 22 g (0.038 mol) of 4-methoxybenzyl 2-[4-(benzenesulphonylthio)-3-tert.-butyloxycarbonylamino-2-oxo-azetidin-1-yl]-3-methylenebutyrate are dissolved in 120 ml of ethyl acetate and 120 ml of water are added. 4 g (0.056 mol) of chlorine gas are then passed in at 0°-5° C. in the course of 10 min. The mixture is subsequently stirred at 0° C. for 30 min., then 8.4 g (0.1 mol) of sodium hydrogencarbonate and 12.4 g (0.05 mol) of sodium thiosulphate pentahydrate are added. After stirring for 10 minutes, the ethyl acetate phase is separated off, dried with magnesium sulphate and evaporated in vacuo. The residue is chromatographed on 300 g of HD-SIL 18-30-60 0.02 to 0.045 mm (Kronwald Separationstechnik GmbH) using an acetonitrile-water 65:35 mixture as the eluent. After evaporating the appropriate fractions in vacuo, the product is obtained as a solid foam.

Yield 15.3 g of product=66% of theory

NMR (250 MHz, CDCl3)1.4[9]s, 3.8[3]s, 4.1[2]q J=12Hz, 4.75[1]s, 4.95-5.15[5]m, 5.2[1]s, 5.8[1]d J=5Hz, 6.9[2]d J=8Hz, 7.3[2]d J=8Hz, 7.5[2]tr J=8Hz, 7.6[1]tr J=8Hz, 7.85[2]d J=8Hz

R$_f$ value: 0.33 (toluene/ethyl acetate 8:2)

EXAMPLE 13

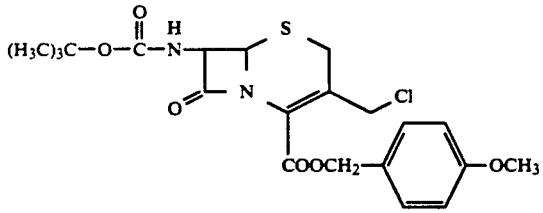

4-Methoxybenzyl 7-tert.-butyloxycarbonylamino-3-chloromethyl-3-cephem-4-carboxylate 15.3 g (0.025 mol) of 4-methoxybenzyl 2-[4-(benzenesulphonylthio)-3-tert.-butyloxycarbonylamino-2-oxo-azetidin-1-yl]-4-chloro-3-methylenebutyrate are dissolved in 50 ml of DMF and added dropwise at −40° C. to a solution of 4.2 ml (0.056 mol) of 25% strength ammonia water in 20 ml of DMF. The mixture is subsequently stirred at −40° C. for 30 min., then 20 ml of 1N hydrochloric acid are added dropwise at −40° C. The reaction mixture is poured into 500 ml of water with stirring and stirred for 1 h. The precipitate formed is filtered off with suction, dissolved in ethyl acetate and washed three times with water.

The ethyl acetate solution is dried using magnesium sulphate and evaporated in vacuo. The residue is chromatographed on 240 g of silica gel Si60 0.04 to 0.063 mm using a toluene/ethyl acetate 95:5 mixture as the eluent After evaporating the appropriate fractions in vacuo, the product is obtained as a solid foam.

Yield: 9.6 g of product = 82% of theory

NMR (250 MHz, CDCl₃): 1.45[9]s, 3.5[1]d, J 18Hz, 3 65[1]d J = 18Hz, 3.8[3]s, 4.4[1]d J 12Hz, 4.55[1]d J 12Hz, 4.95[1]d J = 5Hz, 5.2[1]d J = 10Hz, 5.25[2]s, 5.6[1]dd J = 10Hz, J = 5Hz, 6.9[2]d J = 8Hz, 7.3[2]d J = 8Hz

R_f value: 0.65 (toluene/ethyl acetate 8:2)

EXAMPLE 14

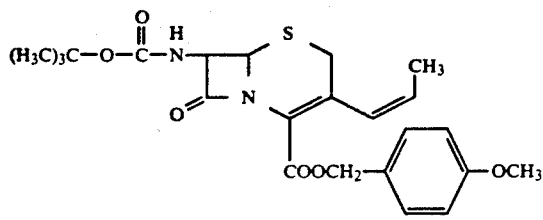

4-Methoxybenzyl 7-tert.-butyloxycarbonylamino-3-(propen-1-yl)-3-cephem-4-carboxylate 9 3 g (0.02 mol) of 4-methoxybenzyl 7-tert.-butyloxycarbonylamino-3-chloromethyl-3-cephem-4-carboxylate are dissolved in 100 ml of dichloromethane. After adding 100 ml of isopropanol, 4.6 g (0.02 mol) of triphenylphosphine and 3.3 g (0.02 mol) of potassium iodide, the reaction mixture is vigorously stirred at 20° C. for 4 h. 22.3 ml (0.4 mol) of acetaldehyde and a solution of 2.76 g (0.02 mol) of potassium carbonate in 100 ml of water are then added. The reaction mixture is stirred vigorously for 1 h, then the phases are separated and the organic phase is dried using magnesium sulphate. The organic phase is evaporated in vacuo, and the residue is crystallized from isopropanol. The precipitate formed is filtered off with suction, washed with isopropanol and dried in vacuo.

Yield: 3.0 g of product (mixture of the Z- and E-isomers in the ratio 1:8) = 33% of theory NMR (200 MHz, DMSO-d₆): 1.4[9]s, 1.5[3]dd J = 7Hz J = 2Hz, 3.55[2]AB system, 3.8[3]s, 5.05[1]d J = 12Hz, 5.1[1]d J = 5Hz, 5.15[1]d J = 12Hz, 5.45[1]dd J = 8Hz J = 5Hz, 5.6[1]dq J = 10Hz J = 7Hz, 6.1[1( d J = 10Hz, 6.9[2]d J = 8Hz, 7.3[2]d J = 8Hz, 8.0[1]d J = 8Hz The NMR data apply to the Z-isomer.

R_f value: 0.64 for the Z-isomer (toluene/ethyl acetate 8:2) 0.67 for the E-isomer (toluene/ethyl acetate 8:2)

EXAMPLE 15

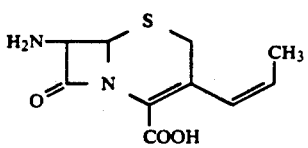

(7-amino-3-(propen-1-yl)-3-cephem-4-carboxylic acid)

2.76 9 (6 mmol) of 4-methoxy-benzyl 7-tert.-butyloxycarbonylamino-3-(propen-1-yl)-3-cephem-4-carboxylate are stirred in 25 ml of trifluoroacetic acid at 20° C. for 3 h. 300 ml of diisopropyl ether are then added dropwise with ice-cooling and the mixture is subsequently stirred for 15 min. The precipitate obtained is filtered off with suction, washed with diisopropyl ether and suspended in 25 ml of water. This aqueous suspension is brought to pH = 8.3 using about 1.5 ml of 25% strength ammonia water. 1 g of active carbon is added to the aqueous suspension and the mixture is filtered The filtrate is brought to pH = 2.5 using about 1 ml of conc. hydrochloric acid. The precipitate formed is filtered off with suction, washed with water and dried in vacuo.

Yield: 1.0 g of product = 69.4% of theory

What is claimed is:

1. A process for the preparation of the compound 7-amino-3[-8 (Z)-1-propen-1-yl]-3-cephem-4-carboxylic acid (7-APCA) having the formula (I)

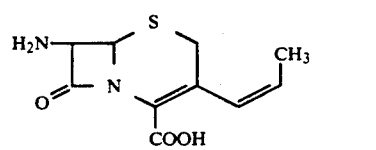

comprising reacting a compound of the formula (II)

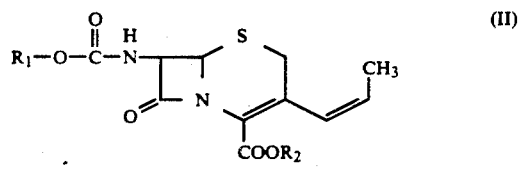

in which $R_1$ and $R_2$ are identical and different and represent a radical selected from the group consisting of alkyl, aryl and aralkyl radicals, with a strong protonic acid or with a Lewis acid.

2. The process according to claim 1 wherein $R_1$ and $R_2$ are independently selected from the group consisting of t-butyl, 1,1-dimethylpropyl, 1,1-diethylpropyl, 1,1-dimethylbutyl, 1,1,2,2-tetramethylpropyl, benzyl, 3,4-dimethoxybenzyl, 3,4,5-trimethoxybenzyl, diphenylmethyl, dimethylphenylmethyl, and di(4-methylphenyl)methyl.

3. The process according to claim 1, wherein the protonic acid is selected from the group consisting of lower alkylcarboxylic acids, formic acid, lower halogenated alkylcarboxylic acids, arylcarboxylic acids, lower alkylsulphonic acids, lower halogenated alkylsulphonic acids and arylsulphonic acids.

4. The process according to claim 1, wherein the Lewis acid is selected from the group consisting of aluminum halides, boron halides, titanium halides, tin halides, silyl halides, and trialkylsilyl halides.

5. The process according to claim 1, wherein the reaction is carried out in the presence of a nucleophilic compound.

6. The process according to claim 1, wherein the reaction is carried out in a solvent.

* * * * *

UNITED STATES PATENT AND TRADEMARK OFFICE
CERTIFICATE OF CORRECTION

PATENT NO. : 5,132,419

DATED : July 21, 1992

INVENTOR(S) : Lanz et al.

It is certified that error appears in the above-identified patent and that said Letters Patent is hereby corrected as shown below: On the title page: Item [56]

Insert -- OTHER PUBLICATIONS: Tetrahedron Letters, Vol. 29, No. 26, pp 3179-3182, 1988 --

Col. 20, line 21   Delete " -8 "

Col. 20, line 47   After " benzyl, " insert -- 4-methylbenzyl, 4-methoxybenzyl, 2,4-dimethylbenzyl, --

Signed and Sealed this

Eighteenth Day of January, 1994

*Attest:*

BRUCE LEHMAN

*Attesting Officer*    *Commissioner of Patents and Trademarks*